United States Patent [19]
Fertel et al.

[11] Patent Number: 5,233,082
[45] Date of Patent: Aug. 3, 1993

[54] METHOD OF MAKING 3-HYDROXY-2,4,5-TRIFLUOROBENZOIC ACID

[75] Inventors: Lawrence B. Fertel, Williamsville; William S. Derwin, Buffalo; Neil J. O'Reilly, Grand Island, all of N.Y.

[73] Assignee: Occidental Chemical Corporation, Niagara Falls, N.Y.

[21] Appl. No.: 976,804

[22] Filed: Nov. 16, 1982

[51] Int. Cl.$^5$ .......................................... C07C 229/00
[52] U.S. Cl. ............................ 562/451; 564/177; 564/179; 562/474
[58] Field of Search ............... 562/451, 474; 564/177, 564/179

[56] References Cited

U.S. PATENT DOCUMENTS

| | | | |
|---|---|---|---|
| 2,923,735 | 2/1960 | Erlenmeyer | 562/451 |
| 3,459,794 | 8/1969 | Tamborski | 562/474 |
| 4,160,015 | 7/1979 | Wiegert | 562/451 |
| 4,831,190 | 5/1989 | Atarca et al. | 562/474 |
| 4,831,190 | 5/1989 | Ataka et al. | 562/474 |

FOREIGN PATENT DOCUMENTS

| | | |
|---|---|---|
| 271275 | 6/1988 | European Pat. Off. . |
| 1-006235 | 1/1989 | Japan . |
| 1-268662 | 10/1989 | Japan . |
| 3-127755 | 5/1991 | Japan . |
| 3-232838 | 10/1991 | Japan . |

Primary Examiner—Paul J. Killos
Attorney, Agent, or Firm—Wayne A. Jones; Richard D. Fuerle; Arthur S. Cookfair

[57] ABSTRACT

Disclosed is a method of making 3-hydroxy-2,4,5-trifluorobenzoic acid. A aqueous solution is prepared of an alkali metal base and a tetrafluorophthalimide. The solution is heated to produce a mixture of a salt of a 4-hydroxy-3,5,6-trifluorophthalamic acid and a salt of a 3-hydroxy-2,4,5-trifluorobenzamide. The solution is neutralized with acid to form a precipitate of the 4-hydroxy-3,5,6-trifluorophthalamic acid and the 3-hydroxy-2,4,5-trifluorobenzamide. The precipitate is reacted with a mineral acid to produce 3-hydroxy-2,4,5-trifluorobenzoic acid.

20 Claims, No Drawings

METHOD OF MAKING 3-HYDROXY-2,4,5-TRIFLUOROBENZOIC ACID

BACKGROUND OF THE INVENTION

This invention relates to a method of making 3-hydroxy-2,4,5-trifluorobenzoic acid (HTBA) from an N-alkyl or N-aryl tetrafluorophthalimide. Specifically, a tetrafluorophthalimide is reacted with a base to produce a mixture of the salts of a 4-hydroxy-3,5,6-trifluoro N-substituted phthalamic acid (HTPA) and a 3-hydroxy-2,4,5-trifluoro N-substituted benzamide (HTB), the base is neutralized to form the HTPA and HTB, and the precipitate is acidified, which forms the HTBA.

U.S. Pat. No. 4,831,190, herein incorporated by reference, discloses a process for making HTBA by reacting tetrafluorophthalic acid with a base to form 4-hydroxy-3,5,6-trifluorophthalic acid, which is then decarboxylated. While that process is not known to be unsatisfactory, the starting material, tetrafluorophthalic acid, is considered to be too expensive for many applications.

SUMMARY OF THE INVENTION

We have invented a process for making HTBA starting with an N-alkyl or N-aryl tetrafluorophthalimide. The tetrafluorophthalimide is reacted with a base to produce a mixture of the salts of two novel compounds, an HTPA and an HTB. This mixture is neutralized with acid which precipitates the mixture of the novel compounds. The precipitate is then reacted with acid to produce the HTBA product. Alternatively, the intermediate compounds need not be isolated, and acid can be directly added to the basic reaction mixture to react it further. The intermediate novel compounds are isomers specifically formed that could not have been predicted on the basis of prior art.

DESCRIPTION OF THE INVENTION

The starting material for the process of this invention is a tetrafluorophthalimide having the general formula

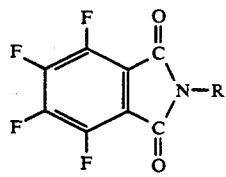

where R is alkyl to $C_8$, cycloalkyl from $C_3$ to $C_8$, or aryl from $C_6$ to $C_{12}$. R is preferably methyl or phenyl as these compounds are less expensive and are easier to work with. This starting material can be produced from tetrachlorophthalic anhydride, a commercially available material sold, for example, by Monsanto as "TETRATHAL ®." The tetrachlorophthalic anhydride reacts with an amine, $RNH_2$, to produce the corresponding imide. Reaction of the imide with fluorinating agents such as, for example, potassium fluoride, produces the starting material of this invention, the tetrafluorophthalimide.

In the first step of the process of this invention, an aqueous solution is prepared of an alkali metal base and a tetrafluorophthalimide. Preferably, a solution is made of the base and the tetrafluorophthalimide is added t the solution. Sodium hydroxide and potassium hydroxide are the preferred bases as they are inexpensive. The solution of the base can be from about 5 to about 50 wt% as less than about a 5 wt% solution may result in incomplete substitution of the hydroxyl for the fluorine on the aromatic ring and more than about a 50 wt% solution of base is unnecessary. Preferably, the solution of the base is about 15 to about 25 wt%. The amount of tetrafluorophthalimide added to the solution of the base can vary from about 5 wt% up to the solubility of the tetrafluorophthalimide in the solution; less than 5 wt% is inefficient. Preferably, the solution of tetrafluorophthalimide is about 10 to about 20 wt%.

The tetrafluorophthalimide is then reacted with the base according to the equation

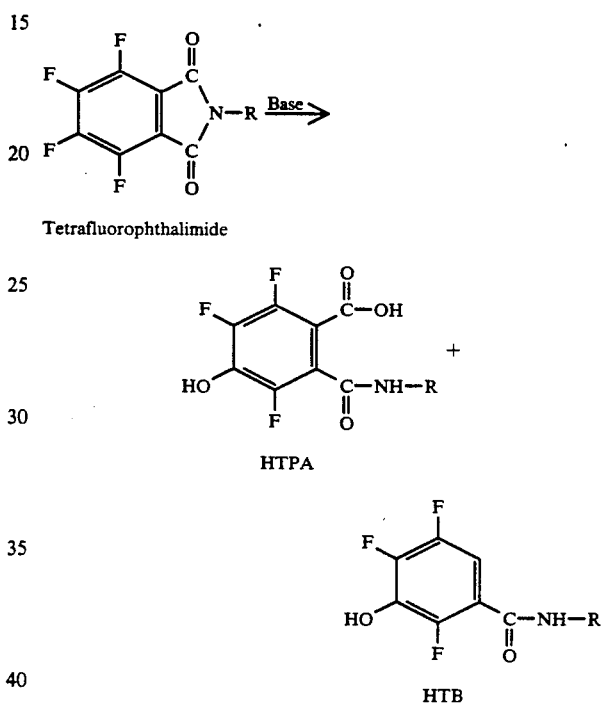

(It is actually the salts of HTPA and HTB that are formed.) This reaction occurs at from about room temperature to about 130° C. Lower temperatures can be used but the reaction tends to be too slow. Lower temperatures also may result in an incomplete reaction and, at temperatures over 130° C., by-products may form. The preferred temperature range is about 75° to about 105° C. The reaction is normally complete after about 2 to about 3 hours and can be followed by gas chromatography (GC) to determine when all the tetrafluorophthalimide has been consumed. The reaction requires at least 2 moles of base per mole of tetrafluorophthalimide and, preferably, about 3 to about 15 moles of base are used per mole of tetrafluorophthalimide to ensure a complete reaction. More than about 15 moles of base per mole of tetrafluorophthalimide is unnecessary and its use means that more base must be subsequently neutralized.

The product of this reaction is a mixture of the salts of an HTPA and an HTB. These compounds and their salts are believed to be novel. While the reaction could produce the other isomers (i.e., 3-hydroxy-2,4,5-trifluorophthalamic acid and 4-hydroxy-3,5,6-trifluorobenzamide) those isomers are not formed.

In the next step of the process of this invention, the solution is neutralized with acid to precipitate a mixture of the HTPA and the HTB. A mineral acid such as hydrochloric acid, sulfuric acid, phosphoric acid, or nitric acid, for example, can be used to neutralize the solution. The pH should be lowered until the precipitate forms. Normally, this requires a pH of about 2.

In the next step of the process of this invention, the precipitate is collected or isolated. This can be accomplished by filtration followed by washing, for example, in cold water. Alternatively, the precipitate can be dissolved in an organic solvent such as ethyl acetate or various ethers to form an organic phase which can be separated from the aqueous phase. The solvent in the organic phase is then evaporated to regenerate the precipitate.

In the next step of the process of this invention, the precipitate is dissolved in an aqueous solution of a mineral acid. Any mineral acid can be used for this purpose including sulfuric acid, hydrochloric acid, nitric acid, and phosphoric acid. A solution of the acid in water is used; for example, about 60% by weight sulfuric acid could be used. Sufficient acid should be used to dissolve the precipitate.

The resulting solution is then heated to a temperature between room temperature and the boiling point of the acid which produces the following reactions:

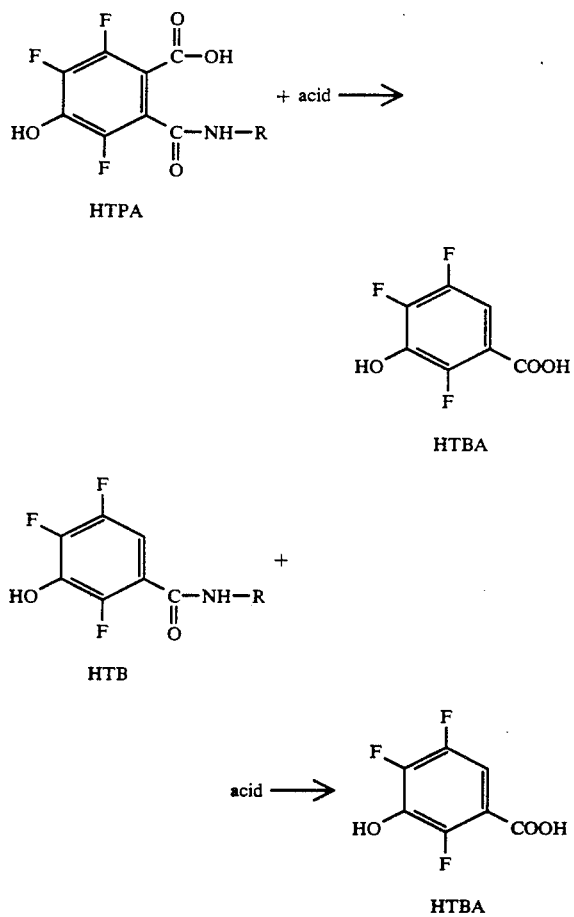

A preferred temperature range is about 125° to about 175° C. This reaction can be performed under pressure but atmospheric pressure is most convenient. The reaction normally takes about 8 hours to complete and can be monitored by gas chromatography until the starting material has been converted. The product, 3-hydroxy-2,4,5-trifluorobenzoic acid, can be recovered by pouring it into water and extracting it into an organic solvent such as ethyl acetate. The organic phase is separated from the aqueous phase and the organic solvent is evaporated to recover the product. As an alternative procedure, following the reaction of the phthalimide with base, the intermediates need not be isolated. By adding sufficient acid to neutralize the base directly as well as to make an acidic solution concentrated enough to effect the hydrolysis and decarboxylation described above, the entire reaction sequence can be accomplished in one reaction vessel. The conditions for this procedure are similar to those described above for the two-step procedure, and the novel intermediates formed in the two-step procedure are the same ones formed in the one-step procedure where they are not isolated. This is shown in Examples 5, 6, and 7.

The product is useful as an intermediate in preparing quinolone antibacterials such as "OFLOXACIN." U.S. Pat. No. 4,831,190 gives additional information on the utility of this product.

The following examples further illustrate this invention.

EXAMPLE 1 Preparation of Phthalimide and Benzamide

Tetrafluoro-N-methyl phthalimide (5.01 g) was added to a solution of potassium hydroxide (10.0 g) in water (50 mL) preheated to 90° C. The reaction was stirred at this temperature for 2 hours, at which time it was cooled to room temperature. Water (100 mL) was added, and the resultant solution was acidified to pH 1.5 with the addition of concentrated hydrochloric acid. Extraction with 4×25 mL of ethyl acetate, followed by drying over magnesium sulfate and removal of the solvent led to 3.52 g of solid material. An additional 1.92 g of material was recovered by reacidification of the aqueous layer, followed by extraction described above. A total of 5.44 g of solids were recovered. Analysis of the solids by gas chromatography/mass spectroscopy (GCMS) and $^{19}F$ nuclear magnetic resonance (NMR) indicated a mixture of 73% 4-hydroxy-3,5,6-trifluoro-N-methylphthalamic acid and 24% 3-hydroxy-2,4,5-trifluoro-N-methylbenzamide.

EXAMPLE 2 Use of N-Phenyl Protecting Group

Tetrafluoro-N-phenylphthalimide (5.01 g) was added to a solution of potassium hydroxide (10.0 g) in water (50 mL) preheated to 95° C. The reaction was stirred at this temperature for 2 hours. Analysis of the solid by GCMS and $^{19}F$ NMR indicated a mixture of 92% 4-hydroxy-3,5,6-trifluoro-N-methylphthalamic acid and 8% 3-hydroxy-2,4,5-trifluoro-N-methylbenzamide.

EXAMPLE 3 Use of Sodium Hydroxide

Tetrafluoro-N-methylphthalimide (0.5 g) was added to a solution of sodium hydroxide (1.0 g) in water (5 mL). The mixture was heated at 94° C. for 3 hours at which time analysis of the reaction by GC showed complete consumption of the starting material and formation of a mixture comprising as the major species, 62% 4-hydroxy-3,5,6-trifluoro N-methylphthalamic acid and 28% 3-hydroxy-2,4,5-trifluoro-N-methylbenzamide.

EXAMPLE 4 Preparation of 3-Hydroxy-2,4,5-Trifluorobenzoic Acid

Mixed together were 4.74 g of the solids product of Example 1 and 20 mL of 60% (w/w) aqueous sulfuric acid. The reaction was stirred and heated at 150° C. for 8 hours. The reaction was then cooled to room temperature and poured into 100 mL of water. Extraction with 4×25 mL of ethyl acetate, followed by drying the organic layer over magnesium sulfate and solvent removal, led to 2.94 g of a solid. Analysis by GCMS and $^{19}F$ NMR indicated the solid was the desired 3-hydroxy-2,4,5-trifluorobenzoic acid.

EXAMPLE 5 Hydrolysis/Decarboxylation at Atmospheric Pressure with Sulfuric Acid Tetrafluoro-N-methylphthalimide (5 g) was added to a solution of potassium hydroxide (4.98 g) in water (25 mL). The solution was stirred and heated at 95° C. for 6 hours, at which time GC analysis showed consumption of the starting material and formation of HTPA and HTB. The solution was cooled in an ice bath to near 0° C. and concentrated $H_2SO_4$ was added (45.2 g) which precipitated a mixture of HTPA and HTB. The mixture was heated to 145° C. for 1 hour which dissolved the precipitate, and then an additional 5.06 g of concentrated acid was added. Heating was continued for an additional 5 hours, at which time a GC showed complete consumption of the reaction intermediates. The solution was cooled to room temperature and quenched into 100 mL of water. After extraction with 3×50 mL of ethyl acetate, the combined organic layers were washed with water and dried over magnesium sulfate. Evaporation of the solvent led to 3.97 g of 3-hydroxy-2,4,5-trifluorobenzoic acid.

EXAMPLE 6 Hydrolysis/Decarboxylation at Atmospheric Pressure with HCl

Tetrafluoro-N-methylphthalimide (5 g) was added to a solution of sodium hydroxide (3 g) in water (10 mL) preheated at 90° C. The reaction was heated with stirring at 95° C. for 3.5 h, at which time GC analysis showed complete consumption of the starting material and formation of HTPA and HTB. After cooling in an ice bath, 10 mL of concentrated hydrochloric acid was added which precipitated a mixture of HTPA and HTB, and the reaction was heated at 125° C. for an additional 15 h which dissolved the precipitates. Analysis of the reaction mixture indicated formation of 3-hydroxy-2,4,5-trifluorobenzoic acid as the major species.

EXAMPLE 7 Hydrolysis/Decarboxylation at Elevated Pressures with HCl

Tetrafluoro-N-methylphthalimide (31.5 g) was added to a solution of sodium hydroxide (19 g) in water (63 mL). The mixture was heated at 95° C. for 6 h. GC showed the formation of HTPA and HTB. After cooling to room temperature, the contents of the reaction was added to an autoclave, and concentrated hydrochloric acid (70 mL) was added which precipitated the HTPA and HTB. The mixture was stirred at 150° C. for 6 h. which dissolved the precipitate. After cooling to room temperature and venting the $CO_2$ produced, the solution was extracted with 2×100 mL of butyl acetate. After separation, the butyl acetate was removed, leading to 24.5 g of HTBA.

We claim:

1. A method of making 3-hydroxy-2,4,5-trifluorobenzoic acid comprising
   (A) preparing an aqueous solution of an alkali metal base and a tetrafluorophthalimide having the general formula

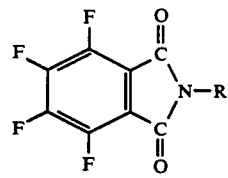

where R is alkyl or cycloalkyl to $C_8$ or aryl to $C_{12}$;
   (B) reacting said base with said tetrafluorophthalimide to produce a mixture of a salt of a 4-hydroxy-3,5,6-trifluorophthalimic acid having the formula

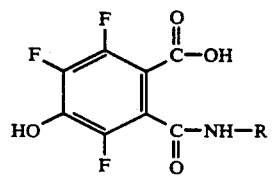

and a salt of a 3-hydroxy-2,4,5-trifluorobenzamide having the formula

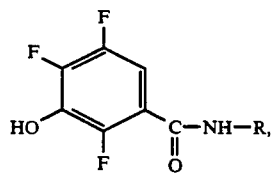

(C) neutralizing said solution to precipitate said 4-hydroxy-3,5,6-trifluorophthalamic acid and said 3-hydroxy-2,4,5-trifluorobenzamide; and
   (D) reacting said 4-hydroxy-3,5,6-trifluorophthalamic acid and said 3-hydroxy-2,4,5-trifluorobenzamide with acid to produce said 3-hydroxy-2,4,5-trifluorobenzoic acid.

2. A method according to claim 1 wherein R is methyl.

3. A method according to claim 1 where R is phenyl.

4. A method according to claim 1 wherein said alkali metal base is sodium hydroxide or potassium hydroxide.

5. A method according to claim 1 wherein the concentration of said alkali metal base is about 3 to about 15 moles per mole of said tetrafluorophthalimide.

6. A method according to claim 1 wherein said precipitate is not isolated.

7. A method of making 3-hydroxy-2,4,5-trifluorobenzoic acid comprising
   (A) adding a tetrafluorophthalimide selected from the group consisting of N-methyl tetrafluorophthalimide and N-phenyl tetrafluorophthalimide to a first aqueous solution of an alkali metal hydroxide, where the concentration of said alkali metal hydroxide is about 3 to about 15 moles per mole of said tetrafluorophthalimide;
   (B) heating said first aqueous solution to a temperature between room temperature and 130° C. to produce a mixture of a salt of the corresponding 4-hydroxy-3,5,6-trifluorophthalamic acid and a salt of the corresponding 3-hydroxy-2,4,5-trifluorobenzamide;

(C) lowering the pH of said first solution to precipitate a mixture of said 4-hydroxy-3,5,6-trifluorophthalamic acid and said 3-hydroxy-2,4,5-trifluorobenzamide;

(D) isolating said precipitated mixture;

(E) forming a second aqueous solution of said precipitated mixture in a mineral acid; and (F) heating said second solution at a temperature between room temperature and the boiling point of said mineral acid until said 3-hydroxy-2,4,5-trifluorobenzoic acid has formed.

8. A method according to claim 7 wherein said tetrafluorophthalimide is N-methyl tetrafluorophthalimide.

9. A method according to claim 7 wherein said tetrafluorophthalimide is N-phenyl tetrafluorophthalimide.

10. A method according to claim 7 wherein, in step (B), said first solution is heated to about 75° to about 105° C.

11. A method according to claim 7 wherein the pH in step (C) is lowered to about 2.

12. A method according to claim 7 wherein, in step (D), said precipitated mixture is isolated by filtration.

13. A method according to claim 7 wherein, in step (D), said precipitated mixture is isolated by extracting it into an organic solvent, separating said organic solvent from said first solution, and evaporating said organic solvent.

14. A method according to claim 7 wherein said second solution is heated, in step (F), at a temperature of about 125° to about 175° C.

15. A compound selected from the group consisting of

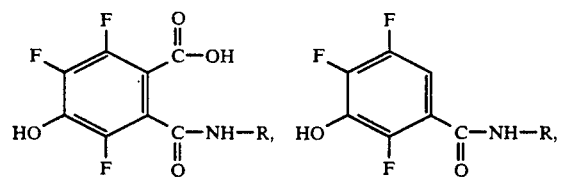

and mixtures and salts thereof, where R is alkyl to $C_8$, cycloalkyl from $C_3$ to $C_8$, or aryl from $C_6$ to $C_{12}$.

16. A compound according to claim 15 having the formula

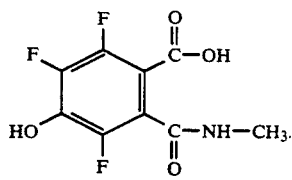

17. A compound according to claim 15 having the formula

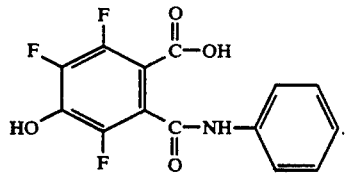

18. A compound according to claim 15 having the formula

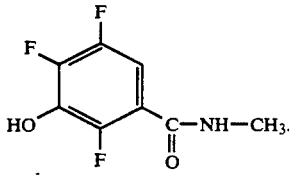

19. A compound according to claim 15 having the formula

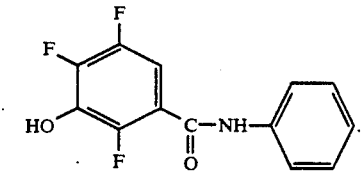

20. An alkali metal salt of a compound according to claim 15.

* * * * *